| United States Patent [19] | | [11] Patent Number: 4,864,039 |
|---|---|---|
| Seto et al. | | [45] Date of Patent: Sep. 5, 1989 |

[54] 3,3'(2H,2'H-SPIROBIBENZOFURAN COMPOUNDS

[75] Inventors: Nobuo Seto; Masakazu Morigaki, both of Minami-ashigara, Japan

[73] Assignee: Fuji Photo Film Co., Ltd., Kanagawa, Japan

[21] Appl. No.: 31,136

[22] Filed: Mar. 30, 1987

[30] Foreign Application Priority Data

Mar. 31, 1986 [JP] Japan .................................. 61-71297

[51] Int. Cl.⁴ ........................................... C07D 493/10
[52] U.S. Cl. ...................................................... 549/344
[58] Field of Search ........................................ 549/344

[56] References Cited

U.S. PATENT DOCUMENTS

| 3,764,337 | 10/1973 | Arai et al. | 96/100 |
|---|---|---|---|
| 3,930,866 | 1/1976 | Oishi et al. | 96/100 |
| 4,054,551 | 10/1977 | Layer et al. | 260/45.8 A |
| 4,113,488 | 9/1978 | Yamada et al. | 96/56 |
| 4,332,886 | 6/1982 | Aoki et al. | 430/551 |
| 4,360,589 | 11/1982 | Kojima et al. | 430/551 |

FOREIGN PATENT DOCUMENTS

| 2165371 | 10/1972 | Fed. Rep. of Germany . |
|---|---|---|
| 2418928 | 11/1974 | Fed. Rep. of Germany . |
| 2361682 | 8/1977 | France . |
| 44521 | 4/1979 | Japan . |
| 478837 | 9/1976 | U.S.S.R. . |
| 2062888 | 5/1981 | United Kingdom . |

Primary Examiner—Richard L. Raymond
Attorney, Agent, or Firm—Birch, Stewart, Kolasch & Birch

[57] ABSTRACT

A novel 3,3'(2H,2'H)-spirobibenzofuran compound is disclosed. The spirobibenzofuran compound has a strong antioxidizing action and is thus useful as an antioxidant for dyes, synthetic polymer products such as rubbers, plastics and the like, and for petroleum. In addition, the compound is effective in preventing fading and discoloration of color photographic images obtained by a subtractive color process.

10 Claims, No Drawings

3,3'(2'H,2H-SPIROBIBENZOFURAN COMPOUNDS

BACKGROUND OF THE INVENTION

(1) Field of the Invention

This invention relates to novel spirobibenzofuran compounds and more particularly, to novel 3,3'(2H,2'H)-spirobibenzofuran compounds useful as an antioxidant and also to antioxidants comprising the same.

(2) Description of the Prior Art

It is well known that dyes, dyestuffs or polymer materials deteriorate by an oxidation reaction with oxygen from the air. A variety of deterioration inhibitors have been developed to prevent such deterioration. Various types of antioxidants are known including, for example, derivatives of hydroxybenzenes such as phenol, hydroquinone and the like, and piperidine derivatives, and the like.

Hydroxybenzenes are described, for example, in U.S. Pat. Nos. 2,735,765, 3,700,,455, 3,764,337, 3,770,431, 3,930,866, 4,138,259 and 4,388,404. Piperidine derivatives are described, for example, in U.S. Pat. Nos. 4,452,884, 4,465,757, 4,465,765 and 4,584,265 and British Pat. No. 1,326,889.

However, these known deterioration inhibitors unsatisfactory for use as a deterioration inhibitor for a color photographic dye or dye image. Accordingly, there is a demand for antioxidants which can improve the stability of the photographic image.

Also, the known deterioration inhibitors did not show any satisfactory effect when used as an antioxidant for natural or synthetic polymers and, thus, there is a demand for powerful antioxidants for this purpose.

SUMMARY OF THE INVENTION

Accordingly, an object of the invention is to provide novel 3,3'(2H,2'H)-spirobibenzofuran compounds having a good antioxidizing action.

Another object of the invention is to provide an antioxidant which shows good properties as a deterioration inhibitor for color photographic dyes and can improve stability of the photographic images.

A further object of the invention is to provide an antioxidant which is also useful as a deterioration inhibitor for natural or synthetic polymer materials.

Other and further objects, features and advantages of the invention will appear more fully from the following description.

DETAILED DESCRIPTION OF THE INVENTION

We have found that 3,3'(2H,2'H)-spirobibenzofuran compounds of the following general formule (I) exhibit good antioxidizing properties and can satisfy the above objects.

The 3,3'(2H,2'H)-spirobibenzofuran compounds of the invention are represented by the following general formula (I)

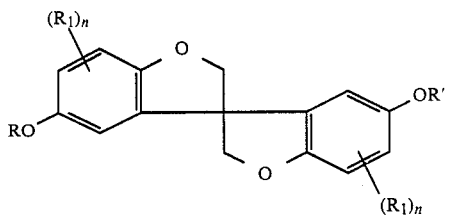

in which R and R' may be the same or different and represent a hydrogen atom or an aliphatic group having not more than 20 carbon atoms. R and R' may, respectively, be a linear, branched or cyclic hydrocarbon group. Preferable aliphatic groups include, for example, straight-chain alkyl group such as, for example, a methyl group, an n-butyl group, an n-octyl group, an n-dodecyl group, an n-tetradecyl group, an n-hexadecyl group and the like; branched alkyl groups such as, for example, an isobutyl group, a 2-ethylhexyl group and the like; and substituted alkyl groups such as, for example, a 2-(n-hexyloxy)ethyl group, a 3,6-dioxadodecyl group, a 1-octylethoxycarbonylmethyl group, a 1-tridecylethoxycarbonylmethyl group and the like. $R_1$ represents an aliphatic group containing not more than 14 carbon atoms, —OR or —OR'. The aliphatic group may be a chain, a branched or a cyclic hydrocarbon group. Preferable aliphatic groups include, for example, straight-chain alkyl group such as a methyl group, an n-butyl group, an n-octyl group, an n-tetradecyl gorup and the like; and branched alkyl group such as an isobutyl group, a t-butyl group, a t-octyl group and the like. In the case where $R_1$ is —OR or —OR', R and R' have, respectively, the same meaning as defined above. n is an integer of from 0 to 3. R or R' and $R_1$ may be joined together to form a ring. When $R_1$ is plural in number, the respective $R_1$'s may be the same or different.

The compounds of the formula in which R and R' are, respectively, a hydrogen atom or an alkyl group are most preferable. The alkyl group for R and R' should preferably have from 1 to 20 carbon atoms.

The 3,3'(2H,2'H)-spirobibenzofuran compounds of the general formula (I) are useful as an antioxidant and especially, as a deterioration inhibitor for polymer materials.

Typical representative examples of the 3,3'(2H,2'H)-spirobibenzofuran compounds of the general formula (I) are exemplified below.

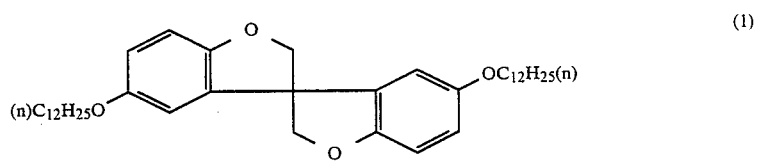

(1)

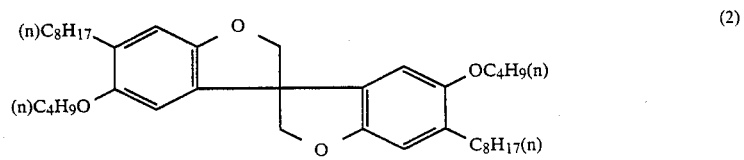

(2)

-continued
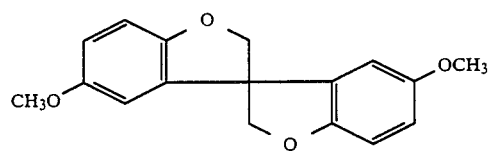
(3)
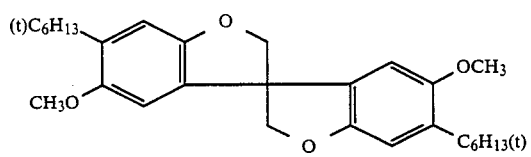
(4)
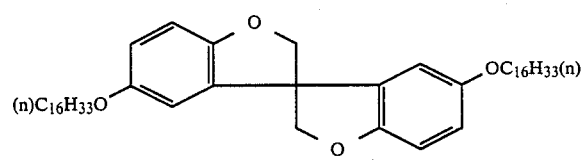
(5)
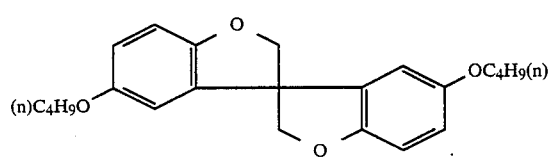
(6)
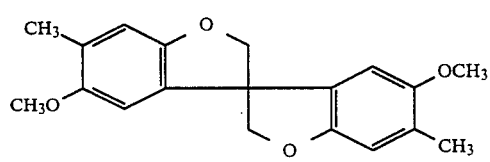
(7)
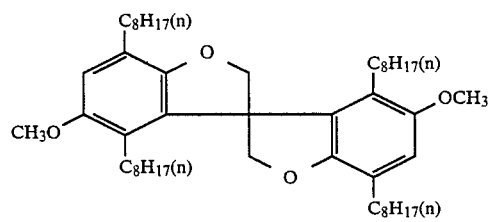
(8)
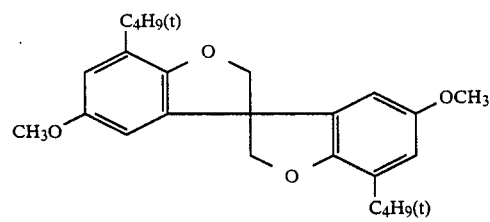
(9)
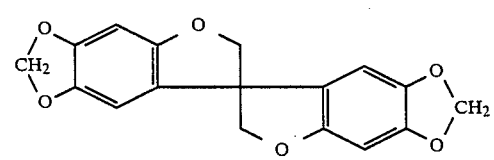
(10)
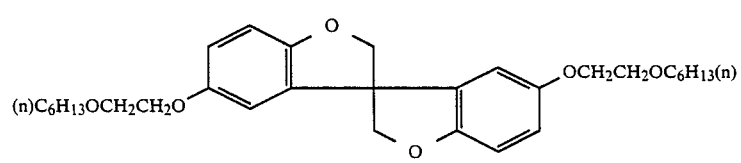
(11)

-continued
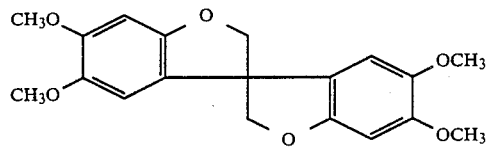 (12)
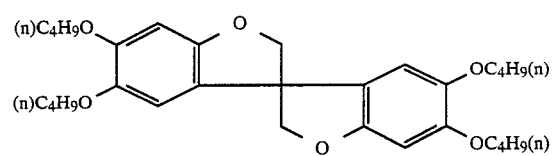 (13)
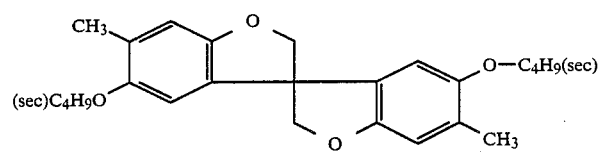 (14)
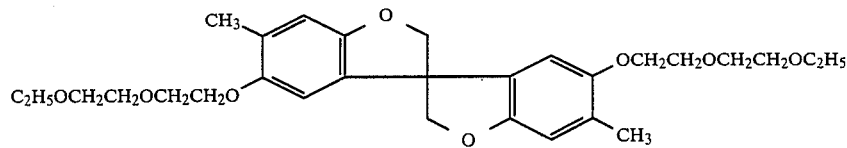 (15)
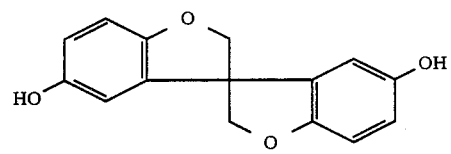 (16)
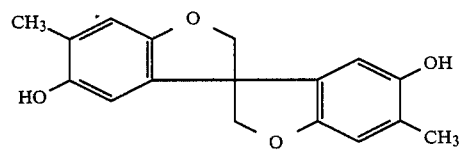 (17)
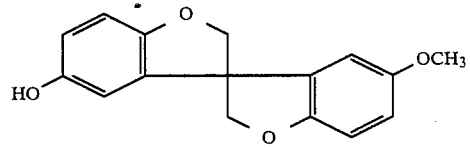 (18)
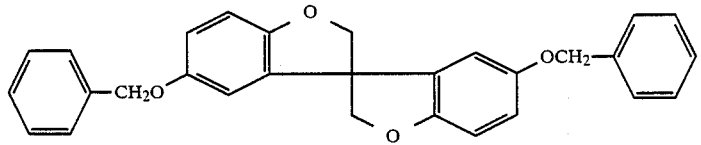 (19)
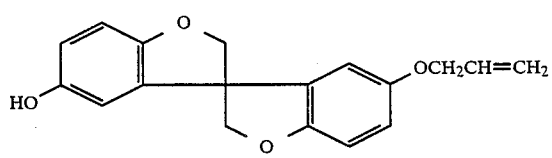 (20)
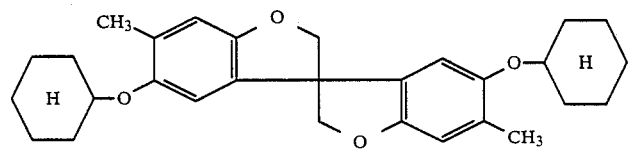 (21)

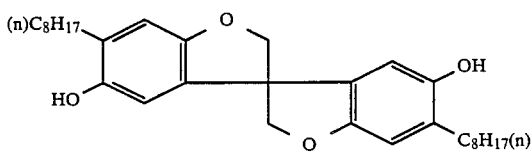

(22)

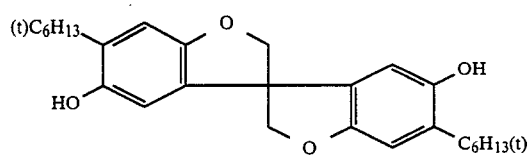

(23)

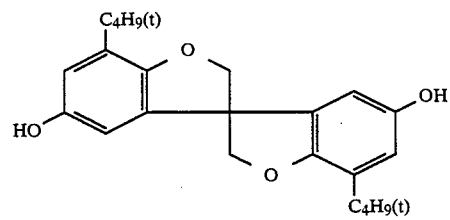

(24)

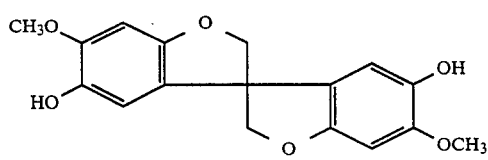

(25)

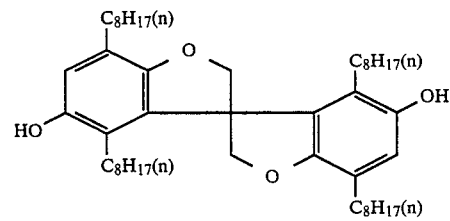

(26)

The 3,3′(2H,2′H)-spirobibenzofuran compounds of general formula (I) are prepared through the following process:

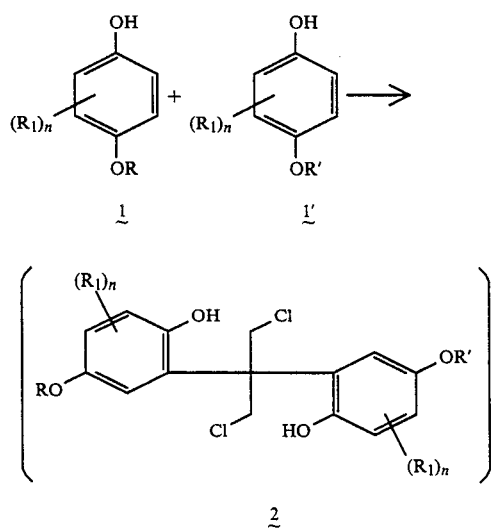

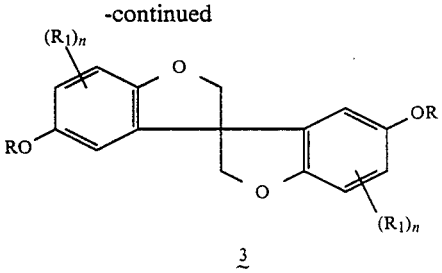

in which R, R′, $R_1$ and n have, respectively, the same meanings as defined before. The compound of the general formula (I) is prepared by reacting p-alkoxyphenol analogues 1 and 1′ with 1,3-dichloro-2-propanone to obtain compound 2 and subjecting compound 2 to intramolecular cyclization to obtain 3,3′(2H,2′H)-spirobibenzofuran compound 3.

In this preparation process, at least one of the ortho positions with respect ot the hydroxyl groups of the phenol compounds 1 and 1′ should be a hydrogen atom. It will be noted that compound 2 is unstable and is, in most cases, impossible to isolate.

The term "antioxidant" used herein is intended to mean not only mixtures of 3,3′(2H,2′H)-spirobibenzofuran compounds as an effective ingredient and suitable diluents, solvents, carriers or the like at arbitrary ratios, but also the spirobibenzofuran compound itself.

The antioxidant of the invention may comprise the compounds of general formula (I) used singly or in combination. Any known antifading agent or color image stabilizer may be used in combination. Preferable known antifading agents include, for example, hydroquinones, 6-hydroxychromans, spirochromans and alkyl ethers thereof. In addition, bisphenols, methylenedioxybenzenes, spiroindanes and N-substituted anilines are also preferred.

The 3,3'(2H,2'H)-spirobibenzofuran compounds of the invention all have a strong antioxidizing action and are thus useful as an antioxidant for dyes, synthetic polymer products such as rubbers, plastics and the like, and for petroleum. In addition, these compounds are effective in preventing fading and discoloration of color photographic images obtained by a subtractive color process.

The invention is more particularly described by way of examples.

Examples 1-3 are synthetic examples of 3,3'(2H,2'H)-spirobibenzofuran compounds of general formula (I) prepared according to the process described before. Examples 4-6 are applications of these 3,3'(2H,2'H)-spirobibenzofuran compounds as an antioxidant.

EXAMPLE 1

Preparation of 5,5'-dimethoxy-3,3'(2H,2'H)-spirobibenzofuran (exemplified compound (3)):

100 ml of methylene chloride was added to 37.2 g (0.30 moles) of p-methoxyphenol, to which 19 g (0,15 moles) of 1,3-dichloro-2-propanpne was further added for dissolution, followed by agitation at 0° C. to 5° C. 9 ml of concentrated sulfuric acid was dropped into the solution in 1 hour and agitated for further 2 hours. The reaction mixture was poured into 200 ml of iced water, to which 200 ml of methylene chloride was added for extraction. After washing twice with 200 ml of cold water, the extract was dried with calcium chloride. After filtration of the calcium chloride, the methylene chloride was distilled off under reduced pressure and the resultant oily substance was subjected to column chromatography to quickly remove unreacted starting materials. 100 ml of benzene was added to the remaining oily substance and agitated at 15° C.-20° C., followed by gradual addition of 2 g (0.083 moles) of sodium hydride. After agitation for 1 hour further, the mixture was cooled down to 0° C. to 10° C. and agitated, during which 20 ml of methanol was dropped in 10 minutes. The reaction mixture was poured into 200 ml of iced water containing 7 ml of concentrated hydrochloric acid. Extraction with 100 ml of ethyl acetate was performed, followed by washing twice with 200 ml of cold water and drying with anhydrous Glauber's salt. After removal of the Glauber's salt by filtration, the ethyl acetate was distilled off under reduced pressure and the resultant oily substance was purified with column chromatography. 40 ml of methanol was added to the thus purified product for crystallization, followed by recrystallization from further 40 ml of methanol to give 9.4 g of exemplified compound (3).

Yield: 22%, m.p.:
1790° C.-180° C.
IR (KBr,cm$^{-1}$);
2940, 2890, 2835, 1602, 1480, 1435, 1270, 1200, 1180
NMR (CDCl$_3$,δ);
6.8~6.6 (4H, m),
6.6~6.5 (2H, m)
4.6 (2H, d, J8.0 Hz),
3.7 (6H, S)
MS (m/e);
284 (M+)

Elementary analysis (for $C_{17}H_{16}O_4$): Found C: 71.78%, H: 5.64% Calculated C: 71.82%, H: 5.67%

EXAMPLE 2

Preparation of 5,5'-dimethoxy-6,6'-dimethyl-3,3'-(2H,2'H)-spirobibenzofuran (exemplied compound (7)):

100 ml of methylene chloride was added to 27.6 g (0.20 moles) of 3-methyl-4-methyoxyphenol, in which 12.7 g (0.10 mole) of 1,3-dichloro-2-propanone was then dissolved, followed by agitation at 0° C. to 5° C. 6 ml of concentrated sulfuric acid was dropped into the reaction mixture in 1 hour and agitated for 1 hour further. The reaction mixture was poured into 200 ml of iced water, to which 100 ml of methylene chloride was added for extraction. After washing twice with 200 ml of cold water, the extract was dried with calcium chloride. After removal of he calcium chloride by filtration, the methylene chloride was distilled off under reduced pressure. The resultant oily substance was subjected to column chromatography to quickly remove unreacted starting materials. 70 ml of benzene was added to the remaining oily substance and agitated at 10° C. to 15° C., to which 1.5 g (0,063 moles) of sodium hydride was gradually added. After agitation for 1 hour further, the mixture was cooled down to 0° C. to 10° C. and agitated, during which 20 ml of methanol was dropped in 10 minutes. The reaction mixture was poured into 200 ml of iced water containing 5 ml of concentrated hydrochloric acid. 100 ml of ethyl acetate was added for extraction, followed by washing twice with 200 ml of cold water and drying with anhydrous Glauber's salt. After removal of the Glauber's salt by filtration, the ethyl acetate was distilled off under reduced pressure and the resultant oily substance was purified with column chromatography. 20 ml of methanol was added to the thus purified product for crystallization, followed by recrystallization from 30 ml of methanol to give 5.9 g of exemplified compound (7).

Yield: 19%, m.p.:
79° C.-80° C.
IR (KBr,cm$^{-1}$);
2930, 2820, 1604, 1485, 1460, 1410, 1300, 1190, 1010
NMR (CDCl$_3$,δ);
6.6 (2H, S), 6.5 (2H, S),
4.6 (2H, d, J=9.0 Hz),
4.4 (2H, d, J=9.0 Hz),
3.7 (6H, S), 2.2 (6H, S)

Elementary analysis (for $C_{19}H_{20}O_4$) Found C: 73.11%, H: 6.47% Calculated C: 73.06%, H: 6.45%

EXAMPLE 3

Preparation of 5,6,5',6'-dimethylenedioxy-3,3'(2H,2'H)-spirobibenzofuran (exemplified compound (10)):

100 ml of methylene chloride was added to 13.8 g (0.10 mole) of 3,4-methylenedioxyphenol, to which was further added 6.35 g (0.05 moles) of 1,3-dichloro-2-propanone for dissolution, followed by agitation at 5° C. to 10° C. 3 ml of concentrated sulfuric acid was dropped into the mixture in 15 minutes, followed by agitation for 4 hours further whereupon crystals precipitated. The thus precipitated crystals were collected by filtration and washed with 50 ml of methylene chloride. The crystals were dissolved in 100 ml of DMAc and agitated at 0° C. to 5° C. 2.4 g (0,10 mole) of sodium hydride was gradually added to the reaction mixture and, after agitation for 1 hour further, 20 ml of methanol was dropped into the mixture in 10 minutes. The reaction mixture was poured into 200 ml of iced water containing 5 ml of concentrated hydrochloric acid and extracted with 300 ml of ethyl acetate, followed by washing twice with 200 ml of cold water and drying with anhydrous Glauber's salt. After removal of the Glauber's salt by filtration, the ethyl acetate was distilled off under reduced pressure to precipitate crystals. 50 ml of methanol was added to the crystals and filtered, followed by recrystallization from 100 ml of ethyl acetate to give 9.8 g of exemplified compound (10).

Yield: 63%, m.p.: 211° C.–213° C.
IR (KBr,cm$^{-1}$);
3025, 2900, 1615, 1500, 1475, 1295, 1160, 1100
NMR (CDCl$_3$,/DMSO-d$_6$,δ);
6.5 (2H, S),
6.4 (2H, S), 5.9 (4H, S),
4.6 (2H, d, J=10.0 Hz),
4.4 (2H, d, J=10.0 Hz),
MS (m/e); 312 (M+)
Elementary analysis (for C$_{17}$H$_{12}$O$_6$): Found C: 65.42%, H: 3.88% Calculated C: 65.39%, H: 3.87%

EXAMPLE 4

10 g of yellow coupler of α-benzoyl-α-(2,4-dioxo-5,5-dimethyl-3-oxazolidinyl)-2-chloro-5-[alpha-(2,4-di-tert-amylphenoxy)butylamido]acetoanilide was dissolved in 10 ml of tricresyl phosphate and 20 ml of ethyl acetate. The solution was emulsified and dispersed in 80 g of a gelatine solution containing 8 ml of a 1% sodium dodecylbenzenesulfonate aqueous solution.

Thereafter, the emulsified dispersion was mixed with 145 g (containing 7 g of Ag) of a blue-sensitive silver chlorobromide emulsion (80 mole% of Br), to which sodium dodecylbenzenesulfonate was added as a coating aid, followed by coating onto a paper support laminated with polyethylene on both sides thereof.

The coated amount of the coupler was set at 400 mg/m$^2$. A gelatine protective layer (1 g/m$^2$ of gelatine) was coated onto the coupler layer to obtain sample A.

In a similar manner, samples were made in which when the emulsified dispersion was prepared, compounds of the invention and compounds for comparison indicated in Table 1 were added, as an antioxidant, in an amount of 50 mole% of the coupler.

These samples were exposed to light at 100 luxes for 1 second and treated with the following solutions.

| Developing solution: | |
|---|---|
| Benzyl alcohol | 15 m |
| Diethylenetriamine pentaacetate | 5 g |
| KBr | 0.4 g |
| Na$_2$SO$_3$ | 5 g |
| Na$_2$CO$_3$ | 30 g |
| Hydroxylamine sulfate | 2 g |
| 4-amino-3-methyl-N—ethyl-N—β-(methane-sulfoneamido)ethylaniline. 3/2H$_2$SO$_4$.H$_2$O | 4.5 g |
| Water to make 1000 ml pH 10.1 | |
| Bleaching and fixing solution: | |
| Ammonium thiosulfate (70 wt %) | 150 ml |
| Na$_2$SO$_3$ | 5 g |
| Na[Fe(EDTA)] | 40 g |
| EDTA | 4 g |
| Water to make 1000 ml pH 6.8 | |

| Processing: | Temperature | Time |
|---|---|---|
| Developing solution | 33° C. | 3 minutes and 30 seconds |
| Bleaching and fixing solution | 33° C. | 1 minute and 30 seconds |
| Washing with water | 28–35° C. | 3 minutes |

In this manner, a color image was formed on the respective samples. In order to determine the light fastness of the image-bearing samples, each sample was exposed to light from a xenone tester (illumination intensity of 100,000 luxes) through a UV absorption filter, made by Fuji Film Co., Ltd., in order to cut light having wavelengths below 400 nm. The residual dye after the exposure at an initial intensity of 1.5 was indicated by percent.

In order to determine the heat resistance, a residual dye at an initial intensity of 1.5 upon storage at 100° C. for 500 hours in the dark was indicated by percent.

TABLE 1

| Sample Nos. | Antioxidant | Residual Rate of Dye Xenone Light, 200 hrs. | Residual Rate of Dye 100° C., 500 hrs. | Remarks |
|---|---|---|---|---|
| K | | 65% | 90% | blank |
| L | Exemplified compound (08) | 89% | 96% | This invention |
| M | Exemplified compound (18) | 93% | 96% | This invention |
| N | 2,6-di-tert-butyl-4-methylphenol | 71% | 91% | For Comparison |
| O | 2,2,6,6-tetramethyl-4-piperidinol | 69% | 92% | For comparison |

(Described in British Patent No. 1,326.889)

From the results of Example 4, it will be seen that the compounds of the invention exhibit the remarkable antioxidizing action.

EXAMPLE 5

A composition of the following formulation using IIR (Tradename, made by Polyser Co., Ltd., butyl 100 with a degree of unsaturation of 0.7% as a resin base was prepared.

| Polyuser Butyl #100 | 100 parts by weight |
|---|---|
| Hard clay | 120 parts by weight |
| Zinc oxide | 5 parts by weight |
| Stearic acid | 2 parts by weight |
| Sulfur | 1 part by weight |
| Tetramethylthiuram disulfide | 2 parts by weight |
| SRF carbon | 10 parts by weight |
| Mercaptobenzothiazole | 0.5 parts by weight |

This composition was kneaded with rolls, followed by press vulcanization at 160° C. for 45 minutes to obtain a 2 mm thick sheet. The sheet was punched by means of a dumbell die JIS (Japanese Industrial Standards) No. 3 to give a sample piece (a).

Similarly, samples (b)–(f) were made using 1.5 parts by weight of antioxidants indicated in Table 2.

The sample pieces were each placed for deterioration test in a gear oven at 120° C. for 100 hours and subjected to measurements of a tensile strength (Kg/mm$^2$) and an elongation (%). The aging resistance was evaluated according to the ratios (retention, %) to values prior to the aging test. The results are shown in Table 2.

TABLE 2

| Sample | Antioxidant | Aging Characteristics | | Remarks |
|---|---|---|---|---|
| | | Retention of Tensile Strength (%) | Retention of Elongation (%) | |
| a | | 59 | 26 | Blank |
| b | Comparative compound | 72 | 49 | For comparison |
| c | Exemplified compound (3) | 98 | 97 | This invention |
| d | Exemplified compound (7) | 92 | 90 | This invention |
| e | Exemplified compound (16) | 96 | 93 | This invention |
| f | Exemplified compound (17) | 95 | 91 | This invention |

Comparative compound:

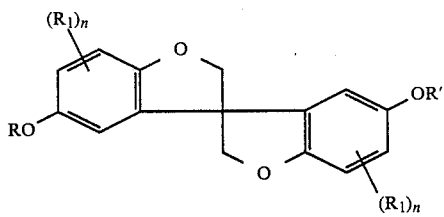

(Compound described in U.S. Pat. No. 3,764,337.)

These results reveal that when used as an antioxidant, the compounds of the invention have a remarkable antioxidizing property than the known compound.

Having described our invention as related to the embodiment, it is our intention that the invention should not be limited by any of the details of the description, unless otherwise specified, but should rather be construed broadly within its spirit and scope as set out in the accompanying claims.

I claim:

1. A 3,3'(2H,2'H)-spirobibenzofuran compound of the following general formula (I)

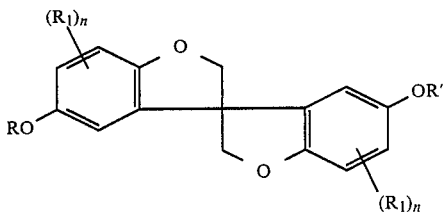

in which R and R' independently represent a hydrogen atom or an aliphatic hydrocarbyl group having not more than 20 carbon atoms, each $R_1$ represents an aliphatic hydrocarbyl group having not more than 14 carbon atoms, —OR or —OR' in which R and R' have, respectively, the same meanings as defined above, or R or R' and $R_1$ may be joined to form a ring, and n is an integer of from 0 to 3, with the proviso that the $(R_1)n$ group does not form an alkylenedioxy ring with R or R' when the $(R_1)n$ group is located in the 4 or 4' position or 6 or 6' position.

2. A 3,3'(2H,2'H)-spirobibenzofuran compound of the following general formula (I)

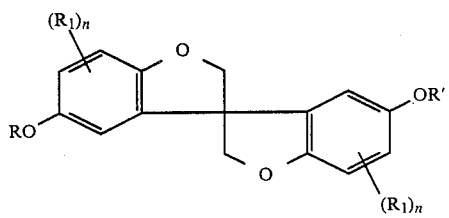

in which R and R' independently represent a hydrogen atom or an alkyl group having not more than 20 carbon atoms, each $R_1$ represents an aliphatic hydrocarbyl group having not more than 14 carbon atoms, —OR or —OR' in which R and R' have, respectively, the same meansings as defined above, or R or R' and $R_1$ may be joined to form a ring, and n is an integer of from 0 to 3, with the proviso that the $(R_1)n$ group does not form an alkylenedioxy ring with R or R' when the $(R_1)n$ group is located in the 4 or 4' position or 6 or 6' position.

3. A 3,3'(2H,2'H)-spirobibenzofuran compound of the following general formula (I)

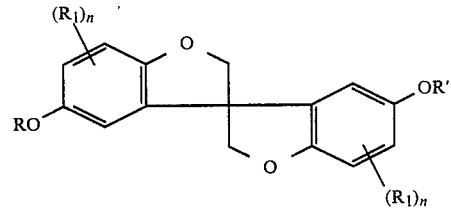

wherein R and R' independently represent a hydrogen atom, a methyl group, an ethyl group, a propyl group, an n-butyl group, an n-octyl group, an n-dodecyl group, an n-tetradecyl group, an n-hexadecyl group, an isobutyl group, a 2-ethylhexyl group, a 2-(n-hexyloxy)ethyl group, a 3,6-dioxyadodecyl group, a 1-octylethoxycarbonylmethyl group, or a 1-tridecylethoxycarbonylmethyl group, each $R_1$ independently represents a hydrogen atom, a methyl group, an n-butyl group, an n-octyl group, an n-tetradecyl group, an isobutyl group, a t-butyl group, or a t-octyl group, —OR or —OR' in which R and R' have, respectively, the same meanings as defined above, or R or R' and $R_1$ may be joined to form a ring, and n is an integer of from 0 to 3, with the proviso that the $(R_1)n$ group does not form an alkylenedioxy ring with R or R' when the $(R_1)n$ group is located in the 4 or 4' position or 6 or 6' position.

4. A 3,3'H(2H,2'H)-spirobibenzofuran compound of the following general formula (I)

in which R and R' independently represent a hydrogen atom or an aliphatic hydrocarbyl group having not more than 20 carbon atoms, each $R_1$ represents an aliphatic hydrocarbyl group having not more than 14 carbon atoms, —OR or —OR' in which R and R' have, respectively, the same meanings as defined above, and n is an integer of from 0 to 3.

5. The 3,3'(2H,2'H)-spirobibenzofuran compound as claimed in claim 1, wherein n is an integer of from 0 to 2.

6. The 3,3'(2H,2'H)-spirobibenzofuran compound as claimed in claim 1, wherein R and R' respectively, is a linear alkyl group, branched alkyl group or cyclic aliphatic hydrocarbon group.

7. The 3,3'(2H,2'H)-spirobibenzofuran compound as claimed in claim 2, wherein n is an integer of from 0 to 2.

8. The 3,3'(2H, 2'H)-spirobibenzofuran compound as claimed in claim 3, wherein n is an integer of from 0 to 2.

9. The 3,3'(2H,2'H)-spirobibenzofuran compound as claimed in claim 2, wherein R, R' and $R_1$ independently represent a hydrogen atom or a methyl group.

10. The 3,3'(2H,2'H)-spirobibenzofuran compound as claimed in claim 3, wherein R, R' and $R_1$ independently represent a hydrogen atom or a methyl group and n is 0 or 1.

* * * * *

UNITED STATES PATENT AND TRADEMARK OFFICE
CERTIFICATE OF CORRECTION

PATENT NO. : 4,864,039
DATED : September 5, 1989
INVENTOR(S) : Nobuo SETO et al.

It is certified that error appears in the above-identified patent and that said Letters Patent is hereby corrected as shown below:

In the title of the specification, please change "3,3'(2H,2'H-SPIRO-BIBENZOFURAN COMPOUNDS" to --3,3'(2H,2'H)-SPIROBIBENZOFURAN COMPOUNDS--

Signed and Sealed this

Thirteenth Day of November, 1990

Attest:

HARRY F. MANBECK, JR.

*Attesting Officer*     *Commissioner of Patents and Trademarks*